(12) United States Patent
Menko (10) Patent No.: US 8,999,370 B2
(45) Date of Patent: Apr. 7, 2015

(54) METHOD TO TREAT AND PREVENT POSTERIOR CAPSULE OPACIFICATION

(75) Inventor: Allyn Sue Menko, Merion Station, PA (US)

(73) Assignee: Thomas Jefferson University, Philadelphia, PA (US)

(*) Notice: Subject to any disclaimer, the term of this patent is extended or adjusted under 35 U.S.C. 154(b) by 943 days.

(21) Appl. No.: 11/913,798

(22) PCT Filed: May 26, 2006

(86) PCT No.: PCT/US2006/020873
§ 371 (c)(1),
(2), (4) Date: Feb. 8, 2008

(87) PCT Pub. No.: WO2006/128152
PCT Pub. Date: Nov. 30, 2006

(65) Prior Publication Data
US 2008/0193504 A1 Aug. 14, 2008

Related U.S. Application Data

(60) Provisional application No. 60/684,745, filed on May 26, 2005, provisional application No. 60/773,888, filed on Feb. 16, 2006.

(51) Int. Cl.
*A61F 2/00* (2006.01)
*A61K 31/136* (2006.01)
*A61K 31/00* (2006.01)
*A61K 31/496* (2006.01)
*A61L 27/54* (2006.01)

(52) U.S. Cl.
CPC .............. *A61K 31/136* (2013.01); *A61K 31/00* (2013.01); *A61K 31/496* (2013.01); *A61L 27/54* (2013.01); *A61L 2300/434* (2013.01); *A61L 2300/602* (2013.01)

(58) Field of Classification Search
CPC ... A61K 31/136; A61K 31/496; A61K 31/00; A61L 2300/602; A61L 2300/434; A61L 27/54
USPC .................................... 514/1.1, 8.2; 424/427
See application file for complete search history.

(56) References Cited

U.S. PATENT DOCUMENTS 6,774,107 B1 * 8/2004 Strittmatter et al. ............ 514/12
6,887,269 B1 5/2005 Hampp et al.

OTHER PUBLICATIONS

Donald Clark, Posterior Capsule Opacification, 11 Curr. Opin. Ophthalmol. 56 (2000).*
Andrea Bonacchi, et al, Signal Transduction by the Chemokine Receptor CXCR3, 276 J. Bio. Chem. 9945 (Mar. 30, 2001).*
Thomas Schindler, et al, Crystal Structure of Hck in Complex with a Src Family-Selective Tyrosine Kinase Inhibitor, 3 Molecular Cell, 639 (May 1999).*
Mark Frey, et al, Epidermal Growth Factor-Stimulated Intestinal Epithelial Cell Migration Requires Src Family Kinase-Dependent p38 MAPK Signaling, 279 J. Bio. Chem. 44513 (Aug. 16, 2004).*
Jaspreet Arora, et al, A Role for 12(s)-HETE in the Response of Human Lens Epithelial Cells to Epidermal Growth factor and Insulin, 37 IOVS 1411, 1416 (1996).*
Wolff, I. M. and A. S. Menko, "Migration of Lens Epithelial Cells on the Posterior Lens Capsule Is Blocked by Inhibition of Src Family Kinases." IOVS 46 E-Abstract 2868, 2005.
Wormstone, I. M. et al., "Identification of Signalling Pathways Involved in Tgfβ2 Induced Matrix Contraction of Human Lens Cells." IVOS 46 E-Abstract 4640, 2005.
Zhou, J. et al., "Inhibition of Src Family Kinases Blocks the Formation of Cortical Cataracts in Cultured Chick Embryo Lenses." ARVO Annual Meeting Abstract Search and Program Planner 2002:2988, 2002.
Zhou, J. et al., "Src Kinase Activation Induces Formation of Lens Opacities through a Pathway Involving p38." ARVO Annual Meeting Abstract Search and Program Planner 2003:3136, 2003.
Jiang, Q. et al., "EGF-Induced Cell Migration Is Mediated by ERK and PI3K/AKT Pathways in Cultured Human Lens Epithelial Cells." Journal of Ocular Pharmacology and Therapeutics 22(2):93-102, 2006.
Zhou, J. and A. S. Menko, "Coordinate Signaling by Src and p38 Kinases in the Induction of Cortical Cataracts" Investigative Ophthalmology & Visual Science 45(7):2314-2323, 2004.
Gong, X. et al., "Development of Cataractous Macrophthalmia in Mice Expressing an Active MEK1 in the Lens" Investigative Ophthalmology & Visual Science 42(3):539-548, 2001.
Wang, E. et al., "Electric Fields and Map Kinase Signaling Can Regulate Early Wound Healing in Lens Epithelium" Investigative Ophthalmology & Visual Science 44(1):244-249, 2003.
Choi et al., Investigative Opthalmology & Visual Science, 45(8):2696-2704 (2004).
Cho et al., Biochemical and Biophysical Research Communications 353:337-343 (2007).
Tholozan, F. et al. The Lens Capsule Protection Against Apoptogens is Cell Specific, ARVO Annual Meeting Abstract Search and Program Planner, vol. 2003, 2003, page Abstract No. 1228 & Annual Meeting for the Association of Research in Vision and Ophthalmology, Ft. Lauderdale, FL, USA; May 4-8, 2003 the whole document.

* cited by examiner

*Primary Examiner* — Brian-Yong Kwon
(74) *Attorney, Agent, or Firm* — David S. Resnick; Shayne Y. Huff (57) ABSTRACT

The invention provides a method to treat or prevent posterior capsular opacification. The method comprises administering a therapeutically or prophylactically effective amount of a pharmaceutical composition comprising at least one kinase inhibitor. The kinase inhibitor inhibits p38 kinases, ERK kinases, and/or Src family kinases. The invention also provides an ocular device coated with at least one kinase inhibitor.

9 Claims, 6 Drawing Sheets

α-SMOOTH MUSCLE ACTIN
DAPI

NORMAL PCO CULTURE         +Src INHIBITOR

*FIG. 4A*

α-SMOOTH MUSCLE ACTIN

DAY 0     DAY 3     DAY 6
DAYS IN CULTURE

FIG. 7

METHOD TO TREAT AND PREVENT POSTERIOR CAPSULE OPACIFICATION

CROSS-REFERENCE TO RELATED APPLICATIONS

This application is a 371 National Stage of International Application No. PCT/US2006/020873 filed on May 26, 2006, which designates the United States, and which claims the benefit under 35 U.S.C. §119(e) of U.S. Provisional Application No. 60/684,745 filed on May 26, 2005, and U.S. Provisional Application No. 60/773,888 filed on Feb. 16, 2006, the entire contents of which are incorporated herein by reference.

GOVERNMENT SUPPORT

The subject matter of this application was made with support from the United States Government, National Institutes of Health (NIH) Grant Nos. EY10577, EY014258 and EY014798. The Government has certain rights to this invention.

BACKGROUND OF THE INVENTION

Cataracts are a lens disorder resulting from the further progression of protein coagulation and calcification. There are four common types of cataracts: senile cataracts associated with aging and oxidative stress, traumatic cataracts which develop after a foreign body enters the lens capsule or following intense exposure to ionizing radiation or infrared rays, complicated cataracts which are secondary to diseases such as diabetes mellitus or eye disorders such as detached retinas, glaucoma and retinitis pigmentosa, and toxic cataracts resulting from medical or chemical toxicity. Regardless of the cause, the disease results in impaired vision and may lead to blindness.

Treatment of such severe lens diseases requires surgical removal of the lens from the capsular bag. The surgical procedure typically involves phacoemulsification, followed by irrigation and aspiration. Implantation of an intraocular lens (IOL) following the extraction of a cataract is now a standard ophthalmic procedure. Current IOLs include rigid, non-deformable lenses as well as rollable or foldable lenses. Furthermore, techniques have been suggested wherein a low viscosity lens material is directly injected into the empty capsular bag and cured in situ as part of the surgical procedure to form an IOL, reducing surgical incisions to about 1 mm. In such a process the capsular bag is used as a mold to form the shape of the lens and thereby contribute to control its refraction.

PCO is the most common postoperative complication of cataract surgery, occurring in 20% to 40% of patients. PCO is a disease caused by epithelial cells in the lens equatorial zone that are not removed during cataract surgery because of their strong adhesion to the matrix components of the lens capsule. Following cataract surgery these epithelial cells migrate onto and across the posterior capsule, eventually populating its entire surface. At a time in the development of PCO not yet specified, these cells lose their epithelial phenotype and become mesenchymal like, a process known as EMT. EMT is characterized the expression of proteins such as α-smooth muscle actin (α-SMA) and fibronectin. α-SMA, a muscle specific cytoskeletal protein, confers these mesenchymal cells with contractile function. The wrinkling of the posterior capsule that occurs in PCO is likely caused by contraction of the epithelial cells following their acquisition of a mesenchymal phenotype. Wrinkling of the capsule is thought to be responsible for the light scattering that causes impaired vision in PCO. Patients with PCO are treated with laser surgery, neodynium:YAG laser posterior capsulotomy, which creates an opening in the opacified posterior capsule and lets light pass through. While this restores vision, it places patients at higher risk for further visual impairment. In addition, the medical costs associated with this procedure are among the highest in the United States.

Accordingly, there is a great need for methods preventing PCO.

SUMMARY OF THE INVENTION

The present invention discloses a novel method for the treatment of posterior lens opacification, a complication arising after cataract surgery. In particular, the invention discloses a method for the prevention of the proliferation, migration and EMT of lens epithelial cells after such surgery by the administration of at least one kinase inhibitor on, in or around an intraocular lens (IOL) implanted during cataract surgery. The kinase inhibitors may inhibit p38 kinase, ERK kinase and/or Src family kinases.

In one embodiment, the kinase inhibitor may coat or be contained within an implant used in conjunction with an IOL.

In one embodiment, the kinase inhibitor may be used with ocular implants inserted for the purpose of vision enhancement.

In one embodiment, the kinase inhibitors may administered as part of an ocular wash solution administered during surgery to remove the cataractous lens and insert the IOL.

In one embodiment, the kinase inhibitor is administered in a time release composition.

In one embodiment, the p38 inhibitor is SB203580 or SB202190.

In one embodiment, the ERK kinase inhibitor is U0126 or PD98059.

In one embodiment, the Src family kinase inhibitor is PP1, SKI606 or SU6656.

BRIEF DESCRIPTION OF THE DRAWINGS

FIGS. 4A-4B show α-SMA, a marker of epithelial to mesenchymal transition, is expressed by day 6 in culture in untreated cultures.

DETAILED DESCRIPTION OF THE INVENTION

The present invention is based on the finding that administration of Src family, p38 and/or ERK kinase inhibitors to a chick organ culture model of PCO prevents the occurrence of PCO. Accordingly, the present invention provides a method to prevent PCO by the administration to the lens of at least one Src family kinase, p38 and/or ERK kinase inhibitor.

The eye of a mammal is composed of a cornea, or clear outer tissue, which refracts light rays en route to the pupil, an iris which controls the size of the pupil, thus regulating the amount of light entering the eye, and a lens which focuses the incoming light through the vitreous fluid to the retina. The lens is embedded in a capsular bag. In the perfect eye, the light path from the cornea, through the lens and vitreous fluid to the retina is unobstructed. Any obstruction or loss in clarity within these structures causes scattering or absorption of light rays, resulting in diminished visual acuity. For example, the lens is susceptible to oxidative damage, trauma and infection.

As the body ages, the effects of oxidative damage accumulate, resulting in loss of lens flexibility and in denatured proteins that slowly coagulate, reducing lens transparency. The natural flexibility of the lens is essential for focusing light onto the retina by the process of accommodation. Accommodation allows the eye to adjust the field of vision for objects at different distances.

The kinase inhibitor can be administered during the procedure to remove the cataract thereby presenting the need for subsequent procedures such as YAG laser capsulotomy. Extracapsular cataract extraction entails the formation of an incision through the eye in order to provide direct access to the anterior chamber of the eye. Although the necessary incision is usually formed at the limbus of the eye, alternative locations for this incision may be selected at the discretion of the surgeon. Following the formation of the incision, a surgical instrument is introduced though the incision into the anterior chamber of the eye. The instrument is then advanced though the anterior chamber such that a cutting surface thereof is in the eye's anterior chamber and in direct contact with the anterior surface of the lens capsule. A capsulorhexis procedure is then performed, wherein a portion of the anterior membrane of the lens capsule is excised in order to provide direct access to the cataractous lens. The cataractous lens is removed from the lens capsule of the eye (aphakia). It will be appreciated that a variety of procedures can be used to remove the cataractous lens, including phacoemulsification and laser ablation. Upon removal of the cataractous lens from the lens capsule, an IOL implant is inserted into the now aphakic eye for the purpose of mimicking the refractive characteristics of a natural lens. IOL implants are often placed within the remaining portions of the lens capsule.

The subject IOL implant may be implanted in an aphakic eye to mimic the refractive characteristics of a healthy natural lens. Surgical methods of implanting an IOL implant in an aphakic eye are well known to those skilled in the art as described in U.S. Pat. Nos. 4,955,889 and 4,957,505 each incorporated herein in its entirety by reference. In the methods of the present invention, the kinase inhibitor can be delivered simultaneously, prior to, or after the IOL is implanted.

As used herein, the language "ocular device" is intended to include devices that are implanted into the eye, including but not limited to, IOLs, capsular tension rings, keratoprostheses, pupil occluders, curable liquids that solidify in situ in the lens capsulary bag, and refractive lens implants and replacements such as phakic intraocular contact lenses, bifocal phakic lens implants, iris-fixated intraocular contact lenses, accommodative intraocular lens implants and posterior chamber phakic intraocular contact lens. An ocular device further includes non-implantable contact lenses and ocular washes administered during surgery to implant an ocular device.

The kinase inhibitor can also be provided on an ocular device, such as a lens that will be implanted within a subject's eye, or a contact lens applied to the exterior surface of an eye. Implantable lenses include any IOL used to replace a patient's diseased lens following cataract surgery, including but not limited to those manufactured by Bausch and Lomb (Rochester N.Y.), Alcon (Fort Worth Tex.), Allergan (Irvine Calif.), Ophthalmic Innovations International (Ontario Calif.) and Advanced Medical Optics (Santa Ana Calif.). The invention further provides a lens system or ocular device for a therapeutic replacement lens ready for surgical implantation in a subject. When the ocular device is implanted within the lens capsule, the kinase inhibitor is present on the surface or within the structure of the ocular implant provides therapeutic effects (e.g., anti-proliferative effects, anti-migratory, anti-inflammatory effects, etc) to the eye.

The subject IOL implant of the present invention may be manufactured in any configuration acceptable to those skilled in the art for the intended purpose of replacing a natural lens. The IOL implant may be of a plate-style configuration as described in U.S. Pat. Nos. 4,664,666 and 4,936,850 each incorporated herein in its entirety by reference, or of a haptic-style configuration as described in U.S. Pat. Nos. 4,822,358, 4,842,600 and 4,863,464 each incorporated herein in its entirety by reference. Any suitable lens configuration is equally suitable for use in the present invention.

The IOL implant of the present invention may be formed from one or more of any number of acceptable materials known to those skilled in the art of IOL manufacture, for example, including but not limited to, polymethylmethacrylate (PMMA), acrylics, silicones, hydrogels or a combination thereof. The IOL may be made of hydrophobic or hydrophilic material. The type of material determines whether the lens cannot fold, is rigid and requires a large incision to insert, or is flexible to allow the lens to be rolled, compressed, or folded for insertion through a smaller incision. The most common materials used in lenses are various chemical modifications of silicon, hydrophobic acrylates, hydrophobic acrylates, and hydrogels which contain water to impart gel-like characteristic to the material. The IOLs made in accordance with the teachings of the present invention can be shaped by machines or cast in configurations providing IOLs with sharp edges, which is medically desirable. Each of these can be formulated or treated to contain a solution containing a kinase inhibitor or coated with a composition containing a kinase inhibitor.

In another embodiment, the form of the ocular device of the present invention can be a substantially circular ("O") ring or loop capable of fitting into the lens capsule in conjunction with an IOL. The O ring or loop has approximately the diameter of the lens and is placed in the eye so as to go around the inner periphery of the capsule. After the device is in place, an IOL is inserted.

The invention also provides a method of using a kinase inhibitor coated ocular implant of this invention in the treatment of myopia, hyperopia or presbyopia, wherein the implant is surgically implanted in the phakic eye to compensate for refractive errors. The implant may subsequently be removed from the eye, if necessary.

In another embodiment, the coating comprising the kinase inhibitor does not cover the entire surface of the implant. The coating is preferably in contact with the interior surface of the capsular bag to form a continuous ring of interfacial contact, preferably around the equatorial zone. The coating may also cover the haptic of a lens forming a continuous ring for contact with the interior surface of the capsular bag, or it may coat a capsular tension ring which is inserted into the capsular bag and provides anatomical support for weak or damaged lens capsules around the equatorial zone. Any combination of coating locations as described herein is contemplated by the invention.

Alternatively the implant may form a lining for the lens capsule and be formed by introducing a curable liquid which cures in situ to form the implant and provides an overall interface for the capsule inner surface and derivatized implant. Alternatively, the implant may be a gel or elastomeric material used to form a "phaco-ersatz lens" (Parel et al., Graefe's Arch. Clin. Exp. Opthalmol. (1986) 224, 165 et seq) which substantially fills the capsule. Suitable polymers are silicone oils and elastomers cross-linked hydrophilic polymers such as naturally occurring polymers, polyurethanes, hydrophilic and hydrophobic polyacrylic compounds. The coating may, in all these applications, be substantially permanently bound to (or immobilized on) the implant surface. Any combination of coating locations as described herein is contemplated by the invention.

In one embodiment of the invention, an irrigating or volume replacement solution, e.g. an ocular wash, containing at least one kinase inhibitor is administered to the capsule with or before inserting the replacement lens. Alternatively, the kinase inhibitor may be contained within as an ocular wash solution used, for example, to clear the surgical field during intraocular surgery.

In one embodiment, the contact lens or implantable IOL is packaged in an ophthalmically acceptable medium which contains the kinase inhibitor. For example, a porous hydrogel lens (e.g., Hydroview™, Bausch & Lomb Surgical, Rochester N.Y.) retains the kinase inhibitor within the pores. Upon application of the contact lens or insertion/implantation of the lens into the lens capsule, the kinase inhibitor is released. An ocular device containing agent(s) in a slow-release system provides extended therapy, for example, over a post-surgical recovery period as the actives are slowly released through the porous elements.

In another embodiment, a contact lens or implantable lens is coated to provide the kinase inhibitor. This embodiment may be used with a non-hydrogel hydrophilic lens, a hydrophobic lens, a lens made from an acrylic material (e.g., AcrySof™; Alcon, Fort Worth Tex.; Sensar™; Advanced Medical Optics, Santa Ana Calif.), a silicone lens (e.g., CeeOn™, Pharmacia & Upjohn Company, Pickering Ohio.), etc. Coating and/or incorporation procedures that may be used are known to one skilled in the art; for example, as disclosed in U.S. Pat. Nos. 6,238,799; 6,179,817; 6,306,422; 6,258,856; 6,858,222; 6,673,453; 6,106,554; 6,143,028; 6,063,396 and U.S. Patent App. No. 2003/0208013, each of which is incorporated by reference herein in its entirety. The kinase inhibitor may be added to the storage solution during packaging of the lens, or may be incorporated into the manufacture of the lens. For example, the kinase inhibitor may be incorporated into either or both the hydration fluid in the formation of a hydrophilic or hydrogel lens, or in the storage solution. In another example, the kinase inhibitor may be in an acceptable encapsulated form in a hydrogel IOL for extended long term release.

The kinase inhibitor may be formulated with a viscoelastic substance such as hyaluronic acid, or may be contained in microspheres, macrospheres, microvesicles, macrovesicles, microcapsules, macrocapsules, liposomes, etc., as described in U.S. Pat. App. No. 2005/0025810, which is expressly incorporated by reference herein in its entirety. This embodiment may be used with solutions administered to prevent posterior capsular opacification following cataract surgery, as previously described.

Liposomes may be prepared from dipalmitoyl phosphatidylcholine (DPPC), for example, from egg phosphatidylcholine (PC), a lipid with a low heat of transition. Liposomes are made using standard procedures as known to one skilled in the art. The kinase inhibitor, in amounts ranging from nanogram to microgram quantities, or higher, is added to a solution of egg PC, and the lipophilic drug binds to the liposome A time-release drug delivery system may be administered intraocularly to result in sustained release of the kinase inhibitor over a period of time. The formulation may be in the form of a vehicle, such as a micro- or macro-capsule or matrix of biocompatible polymers such as polycaprolactone, polyglycolic acid, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and other polymers such as those disclosed in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety, or lipids that may be formulated as microspheres or liposomes. A microscopic or macroscopic formulation may be administered through a needle, or may be implanted by suturing within the eye, for example, within the lens capsule. As an illustrative example, sirolimus may be mixed with polyvinyl alcohol (PVA), the mixture then dried and coated with ethylene vinyl acetate, then cooled again with PVA. In a formulation for intraocular administration, the liposome capsule degrades due to cellular digestion providing a slow release drug delivery system, allowing the patient a constant exposure to the drug over time.

Delayed or extended release properties may be provided through various formulations of the vehicle (coated or uncoated microsphere, coated or uncoated capsule, lipid or polymer components, unilamellar or multilamellar structure, and combinations of the above, etc.). Other variables may include the patient's pharmacokinetic-pharmacodynamic parameters (e.g., body mass, gender, plasma clearance rate, hepatic function, etc.). The formulation and loading of microspheres, microcapsules, liposomes, etc. and their ocular implantation are standard techniques known by one skilled in the art, for example, the use a ganciclovir sustained-release implant to treat cytomegalovirus retinitis, disclosed in Vitreoretinal Surgical Techniques, Peyman et al., Eds. (Martin Dunitz, London 2001, chapter 45); Handbook of Pharmaceutical Controlled Release Technology, Wise, Ed. (Marcel Dekker, New York 2000), the relevant sections of which are incorporated by reference herein in their entirety.

The implant may exhibit a slow, steady-state release of the kinase inhibitor such that the kinase inhibitor remains substantially within the region of the implant. Alternatively, the implant may exhibit a multi-phase release in which the kinase inhibitor is delivered in an initial "burst" of short duration followed by sustained release of lower concentrations. Such a release profile also advantageously minimizes the amount of kinase inhibitor delivered to non-target regions while exposing the target cells in the localized region to an initial exposure that rapidly initiates the desired modulation. The load bound to the support depends on the surface area of the support and the concentration of the kinase inhibitor solution and the time. Using high concentrations, a higher amount of weakly associated kinase inhibitor may come as a burst. The amounts can be varied and the release modified by how extensively the implant is washed prior to use. The implant also advantageously retains sufficient concentrations of the kinase inhibitor to effectively exert contact modulation upon any target cell physically contacting the implant, for at least several days following placement of the implant.

The effectiveness of the implant with associated kinase inhibitor can be determined in a variety of ways. In one embodiment, human lens epithelial cells obtained from surgical specimens or fresh eye bank tissues may be used. In another embodiment mammalian lens epithelial cells or mammalian lens capsule cultures can be used. In a preferred embodiment chick lens capsule cultures prepared according to Liu et al. (Invest Opthalmol Vis Sci. 1996. 37:906-914) and the example below are used. To test the desired effect of inhibition of cell proliferation and/or EMT, particularly of cells which migrate across the posterior aspect of the lens capsule, the implant can be tested using an in vitro cell culture assay in which mammalian cells or chick cells are added to culture wells containing the polymer implants. In one embodiment, an in vivo model of PCO development is used.

In another use of the invention, the tissue(s) and cells of interest are the lens capsule and any associated residual lens epithelial cells following cataract surgery. The kinase inhibitor is used to prevent growth of the residual lens epithelial cells on the lens capsule after removal of a primary cataract. The primary cataract can be of any type, including senile, juvenile and radiation-induced. The polymer implant can inhibit proliferation or migration and/or inhibit the epithelial to mesenchymal transformation of lens epithelial cells which can grow across the optic axis of the posterior lens capsule following removal of the primary cataract. For evaluation of the efficacy of the invention for use in the prevention of secondary cataract following primary extracapsular cataract surgery, an art accepted in vitro model can be used. Cataract surgery is performed in a host animal such as a rabbit according to methods described by Ulrich, et al., ((1993) J. Cat. Refract Surg. 19:462). Following surgery, a polymer implant is inserted into the capsular bag. The implant is crafted in the form of an open loop or ring the diameter of which approximates the lens equatorial diameter. Both ends of the loop are placed inside the bag using techniques common for placement of intraocular lens haptics. Various concentrations of the cell proliferation-modulating, migration-modulating, and/or epithelial-to-mesenchymal-transformation-modulating agent are absorbed to the implant. Following surgery, eyes are observed to determine the effect of the implant on lens epithelial cells proliferating on the posterior capsule surface. At selected times following surgery, animals are sacrificed and the eyes are histologically studied to assess the degree of lens epithelial cell proliferation.

The development of posterior capsule opacification in humans can take from a few months to several years. Clinically, PCO is determined by slit lamp microscopy presenting as the appearance of lens epithelial cells growing on the posterior lens capsule (posterior capsule opacification). This opacification, especially if centrally located, can result in decreased visual acuity. Treatment of PCO is conventionally performed by YAG laser capsulotomy which removes the opacified capsule and restores a clear line of vision resulting in improved visual acuity. When implanted at the time of primary cataract surgery, the ocular implant coated with kinase inhibitor allows for the release of therapeutic concentrations of agents preventing proliferation and/or migration of lens epithelial cells. Slit lamp microscopy can be used to determine whether posterior capsule opacification has occurred. Alternatively, since posterior capsule opacification can lead to a loss of visual acuity, the maintenance of visual acuity at post-cataract surgery levels or a decreased incidence of YAG capsulotomies can be used to determine the efficacy of the implant.

Toxicity and therapeutic efficacy of such compounds can be determined by standard pharmaceutical procedures in cell cultures, organ cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to unaffected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a local concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a kinase inhibitor, (i.e., an effective dosage) ranges from about 1 nanomolar to about 100 micromolar. In one embodiment the effective dose is about 1-5 nanomolar, in another embodiment 5-10 nanomolar, in still another embodiment 10-50 nanomolar, in still another embodiment 5-100 nanomolar, in still another embodiment 100-500 nanomolar, in still another embodiment 500 nanomolar to 1 micromolar, in still another embodiment 1-10 micromolar, in still another embodiment 10-50 micromolar, in still another embodiment 50-100 micromolar. In one embodiment the effective dose is about 10 micromolar. The skilled artisan will appreciate that certain factors may influence the dosage required to effectively treat and thus prevent PCO in a subject, including but not limited to the severity of the disease or disorder, previous treatments, the general health and/or age of the subject, and other diseases present. Moreover, treatment of a subject with a therapeutically effective amount of kinase inhibitor can include a single treatment or can include a series of treatments.

The compositions comprising kinase inhibitors and/or ocular implant can be provided as kits for use in one or more operations. Kits can include a separate polymer implant and growth-modulating agent. The agent can be a concentrate, including lyophilized compositions, and can be provided in vials which may include one or more dosages. Conveniently, single dosages can be provided in sterilized containers. Alternatively, the kits can include a composition prepared for direct use. Generally, the growth-modulating agent is combined with the solid support by assembly of the various components in a sterile environment and the assembly is maintained in an aseptic environment until use. The compositions are preferably stored dried or lyophilized in a sterile container. Excipients may be used to promote stability under these conditions. Generally if the drug is currently stable under these conditions, it will be stable under the same conditions when associated with an implant. Preferably, the implant is kept dry until it is ready for implantation.

The implant coating may include one or more kinase inhibitors and a pharmaceutically acceptable carrier. The implant may be coated with other compounds, including small molecules, nucleic acid compositions, polypeptide or peptide compositions, and polysaccharide compositions such as heparin.

The pharmaceutically acceptable carrier refers to generally available and known pharmaceutical carriers. The formulation of such compositions is well known to persons skilled in this field. Suitable pharmaceutically acceptable carriers and/or diluents include any and all conventional solvents, dispersion media, fillers, solid carriers, aqueous solutions, coatings, anti-bacterial and anti-fungal agents, isotonic, and absorption enhancing or delaying agents, activity enhancing or delaying agents and the like. The use of such media and agents for pharmaceutically active substances is well known in the art, and it is described, by way of example, in Remington's Pharmaceutical Sciences, 18th Edition, Mack Publishing Company, Pennsylvania, USA. Except insofar as any conventional carrier and/or diluent is incompatible with the active ingredient, use thereof in the pharmaceutical compositions of the present invention is contemplated. Supplementary active ingredients including agents having anti-proliferative, anti-migratory, anti-inflammatory, anti-bacterial or anti-fungal activity can also be incorporated into the compositions of this invention.

Mammalian mitogen-activated protein (MAP)1 kinases are serine/threonine kinases that mediate intracellular signal transduction pathways (Cobb and Goldsmith, 1995, J. Biol. Chem., 270, 14843; Davis, 1995, Mol. Reprod. Dev. 42, 459). Members of the MAP kinase family share sequence similarity and conserved structural domains, and include the ERK (extracellular signal regulated kinase), JNK (Jun N-terminal kinase), and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., 1994, Cell 76, 1025; Han et al., 1994, Science 265, 808; Raingeaud et al., 1995, J. Biol. Chem. 270, 7420; Shapiro and Dinarello, 1995, Proc. Natl. Acad. Sci. USA 92, 12230). In contrast, ERKs are activated by mitogens and growth factors (Bokemeyer et al. 1996, Kidney Int. 49, 1187). A distinguishing feature of each of these kinase families is that the ERKs have a TEY amino acid motif, the JNKs or SAP kinases have a TPY amino acid motif, and the p38 MAP kinases have a TGY amino acid motif.

Any component of the ERK pathway is a potential therapeutic target for inhibition in accordance with the present invention. The mechanism of inhibition may be at the genetic level (e.g., interference with transcription or translation) or at the protein level (e.g., binding, competition). Because of their converging function, specific inhibition of ERK1/2 is expected to effectively intercept a wide variety of upstream mitogenic signals. Preferably, the inhibitor of ERK1 and/or ERK2 (ERK1/2) is a specific inhibitor, that either acts on MEK1/2 or ERK1/2 at the genetic level or protein level. Specific inhibition of the ERK pathway has been demonstrated using approaches such as expression of an ERK-specific antisense molecule (Pages G. et al., Proc. Natl. Acad. Sci. USA, 1993, 90: 8319-8323) and sequestration of ERK1/2 in the cytoplasm and therefore preventing ERK nuclear signaling (Brunet A. et al., EMBO J, 1999, 18: 664-674). Either or both approaches may be used in accordance with the present invention. For example, an inhibitor may be utilized that interferes with expression of ERK1 and/or ERK2, or which sequesters ERK 1 and/or ERK2 in the cytoplasm of the cell, preventing nuclear translocation.

p38 includes four different isoforms: p38α MAP kinase (p38α), p38β MAP kinase (p38β), p38γ MAP kinase (p38γ), and p38δ MAP kinase (p38δ). p38α is expressed ubiquitously. A shorter C-terminal truncated form of p38α known as Mxi-2 has also been identified in a yeast two-hybrid screen based on its association with the transcription factor Max. p38β has been shown to have an additional isoform, p38β2 that lacks the 8 amino acid insertion found in p38β. Between these two variants p38β2 is believed to be the major form as p38β is catalytically less active. p38γ and p38δ are 63% and 61% identical to p38α, respectively. p38γ is expressed predominantly in skeletal muscle wherein p38δ is expressed predominantly in testes pancreas, prostate, small intestine, and endocrine tissue.

All p38 homologues and splice variants contain a 12 amino acid activation loop between kinase domain VII and kinase domain VIII. The activation loop includes a Thr-Gly-Tyr motif. Dual phosphorylation of both Thr-180 and Tyr-182 (p38α numbering) in the TGY motif is essential for the activation of p38 resulting in >1000 fold increase in specific activity of these enzymes. Dual phosphorylation can be effected by MKK6, MKK3 and other members of the MAPKK (mitogen activating protein kinase kinase) family and MAPKKK (mitogen activating protein kinase kinase kinase) family, also referred to as the MAP3K family. In particular, MEKK4/MTK1, ASK1, and TAK1 have been identified as upstream activators of MAP3K. Also, TNF-stimulated activation of p38α is believed to be mediated via recruitment of TRAF2 (TNF receptor associated factor) and the Fas adaptor protein, Dazz, which results in the activation of ASK1 and subsequently p38 and JNK. Also, TAK has been shown to activate MKK6 in response to TGF-β and is believed to be associated with TRAF6 in an IL-1-dependent manner suggesting involvement of TAK1 in IL-1-mediated p38 activation. Additionally, mixed lineage of kinase-3 physically associated with MKK3 and MKK6 is believed to be involved in activation of p38 by Ste-20-linked kinases. Also, MEKK3, small G proteins of the Rho family, and active forms of Cdc42 and Racl in mammalian cells have also been shown to activate the p38 pathways (the latter via p21-activation kinase).

As used herein, the language "p38 inhibitor" is intended to include any inhibitor of one or more kinases within the p38 family of kinases. In a preferred embodiment, one or more p38 family kinase inhibitors is used in the methods and ocular devices of the present invention. In one preferred embodiment, the p38 inhibitor is SB203580 or SB202190.

Compounds that have been suggested for the inhibition of p38 include pyridinylimidazoles. See Young P. R., et al., (1997) J. Biol. Chem. 272, 12116-12121; see also Bender, P. E., (1985) J. Med. Chem. 28, 1169-1177. Examples of pyridinylimidazoles that may inhibit p38 include 6-(4'-fluorophenyl)-5-(4'-pyridyl)-2,3-dihydroimi-dazo(2,1-b)-thiazole and its metabolites (sulfoxide, sulfone), analogues, fragments, and mimetics. It has further been suggested that the minimal structure of pyridinylimidazoles, 4-(pyridin-4-yl)-5-phenylimidazole, may be sufficient to inhibit p38. See Gallagher, T F, et al., (1997) Bio-org. Med. Chem. 5, 49-64.

Certain 1,5-diaryl-substituted pyrazole compounds have also been suggested as p38 inhibitors. Such substituted pyrazole compounds are disclosed in U.S. Pat. No. 6,509,361, assigned to Pharmacia Corporation, incorporated herein by reference for all intended purposes. Additional pyrazole derivatives that inhibit p38 are disclosed in U.S. Pat. No. 6,335,336, assigned to G.D. Searle & Co., incorporated herein by reference for all intended purposes.

Other p38 inhibitors include substituted pyridyl, such as those disclosed in U.S. Patent Application Publication No. 2003/0139462, incorporated herein by reference for all intended purposes.

Additional p38 inhibitors are those disclosed in U.S. Pat. No. 6,610,688, assigned to Sugen, Inc., incorporated herein by reference for all intended purposes.

Quinazoline derivatives may also function as p38 inhibitor. Examples of quinazoline derivatives that are p38 inhibitors are disclosed in U.S. Pat. Nos. 6,541,477 and 6,184,226, assigned to Scios Inc., incorporated herein by reference for all intended purposes, and U.S. Pat. Nos. 6,509,363 and 6,635,644, assigned to Vertex Pharmaceuticals Inc., incorporated herein by reference for all intended purposes.

Aryl ureas and heteroaryl analogues may also function as p38 inhibitors. Examples of aryl ureas and heteroaryl analogues that are p38 inhibitors are disclosed in U.S. Pat. No. 6,344,476, assigned to Bayer Corp., incorporated herein by reference for all intended purposes. WO99/32110, published Jul. 1, 1999, describes heterocyclic ureas as p38 kinase inhibitors. WO99/32463, published Jul. 1, 1999, describes urea compounds that inhibit p38 kinase. WO98/52558, published Nov. 26, 1998, describes urea compounds for the inhibition of p38 kinase. WO99/00357, published Jan. 7, 1999, describes the use of urea compounds as inhibitors of p38 kinase. WO99/58502, published Nov. 18, 1999, describes urea compounds as inhibitors of p38 kinase. These and all other references mentioned herein are incorporated by references for all purposes.

Substituted imidazole compounds and substituted triazole compounds may also function as p38 inhibitors. Such compounds are disclosed in U.S. Pat. Nos. 6,560,871 and 6,599,910, respectively, which incorporated herein by reference for all intended purposes.

Additional p38 inhibitors include RWJ-67657 (RW Johnson Pharmaceutical Research Institute); RDP-58 (SangStat Medical Corp.; acquired by Genzyme Corp.); RDP-58; Scios-323 (Scios Inc.); Scios-469 (Scios Inc.); MKK3/MKK6 inhibitors (Signal Research Division); p38/MEK modulators (Signal Research Division); SB-210313 analogs, SB-220025, SB-238039, HEP-689, SB-203580, SB-239063, SB-239065, SB-242235 (SmithKline Beecham Pharmaceuticals); VX-702 and VX-745 (Vertex Pharmaceuticals Inc.); AMG-548 (Amgen Inc.); Astex p38 kinase inhibitors (Astex Technology Ltd.); RPR-200765 analogs (Aventis SA); Bayer p38 kinase inhibitors (Bayer Corp.); BIRB-796 (Boehringer Ingelheim Pharmaceuticals Inc.); Celltech p38 MAP kinase inhibitor (Celltech Group plc.); FR-167653 (Fujisawa Pharmaceutical Co. Ltd.); 681323 and SB-281832 (GlaxoSmithKline plc); LEO Pharmaceuticals MAP kinase inhibitors (LEO Pharma A/S); Merck & Co. p38 MAP kinase inhibitors (Merck research Laboratories); SC-040 and SC-XX906 (Monsanto Co.); Novartis adenosine A3 antagonists (Novartis AG); p38 MAP kinase inhibitors (Novartis Pharma AG); CP-64131 (Pfizer Inc.); CNI-1493 (Picower Institute for Medical Research); RPR-200765A (Rhone-Poulenc Rorer Ltd.); and Roche p38 MAP kinase inhibitors and Ro-320-1195 (Roche Bioscience).

Inhibitors of p38 include N-(3-tert-butyl-1-methyl-5-pyrazolyl)-N'-(4-(4-pyridinylmethyl)phenyl)urea, RPR 200765A, SB203580, SB202190, UX-745, UX-702, UX-850, and SC10-469 are exemplary p38 inhibitors. Other p38 inhibitors are described in U.S. Pat. Nos. 5,716,972, 5,686,455, 5,656,644, 5,593,992, 5,593,991, 5,663,334, 5,670,527, 5,559,137, 5,658,903, 5,739,143, 5,756,499, 5,716,955, WO 98/25619, WO 97/25048, WO 99/01452, WO 97/25047, WO 99/01131, WO 99/01130, WO 97/33883, WO 97/35856, WO 97/35855, WO 98/06715, WO 98/07425, WO 98/28292, WO 98/56377, WO 98/07966, WO 99/01136, WO 99/17776, WO 99/01131, WO 99/01130, WO 99/32121, WO 00/26209, WO 99/58502, WO 99/58523, WO 99/57101, WO 99/61426, WO 99/59960, WO 99/59959, WO 00/18738, WO 00/17175, WO 99/17204, WO 00/20402, WO 99/64400, WO 00/01688, WO 00/07980, WO 00/07991, WO 00/06563, WO 00/12074, WO 00/12497, WO 00/31072, WO 00/31063, WO 00/23072, WO 00/31065, WO 00/35911, WO 00/39116, WO 00/43384, WO 00/41698, WO 97/36587, WO 97/47618, WO 97/16442, WO 97/16441, WO 97/12876, WO 98/7966, WO 98/56377, WO 98/22109, WO 98/24782, WO 98/24780, WO 98/22457, WO 98/52558, WO 98/52941, WO 98/52937, WO 98/52940, WO 98/56788, WO 98/27098, WO 99/00357, WO 98/47892, WO 98/47899, WO 99/03837, WO 99/01441, WO 99/01449, WO 99/03484, WO 95/09853, WO 95/09851, WO 95/09847, WO 95/09852, WO 92/12154, WO 94/19350, WO 99/15164, WO 98/50356, DE 19842833, JP 2000 86657, and U.S. Patent Application Publication Nos. 20040092547, 20040082551, 20040077682, 20040077647, 20040053923, 20040053958, 20040053942, 20040044044, 20040023992, 20030216446, 20030203905, 20030195355, 20030149041, 20030149037, 20030144529, 20030144520, 20030139462, 20030134888, 20030130319, 20030100756, 20030100588, 20030096817, 20030092717, 20030083327, 20030078432, 20030078275, 20030078166, 20030073687, 20030064982, 20030064981, 20030055068, 20030055044, 20030036543, 20030004164, 20030004161, 20020156114, 20020156081, 20020115671, 20020103245, 20020086869, 20020019393, 20020016477, 20020013354, 20020010170, 20010025044, and 20010044538. p38 inhibitors are also described in Rupert et al., Bioorg Med Chem. Lett. 13:347-50 (2003); Dumas et al., Bioorg Med Chem. Lett. 12:1559-1562 (2002); Dumas et al., Bioorg Med Chem. Lett. 10:2051-2054 (2000); Redman et al., Bioorg Med Chem. Lett. 11:9-12 (2001); Wan et al., Bioorg Med Chem. Lett. 13:1191-4 (2003); Regan et al., J. Med. Chem. 45:2994-3008 (2002); Liverton et al., J. Med. Chem. 42:2180-90 (1999); Dumas, Curr. Opin. Drug Discov. Devel. 5:718-27 (2002); Stelmach et al., Bioorg. Med. Chem. Lett. 13:277-80 (2003); Cirillo et al., Curr. Top. Med. Chem. 2:1021-35 (2002); Pargellis et al., Curr. Opin. Investig. Drugs. 4:566-71; Dumas et al., Bioorg. Med. Chem. Lett. 10:2047-50 (2000); Trejo et al., J. Med. Chem. 46:4702-13 (2003); Mclay et al. Bioorg. Med. Chem. 9:537-54 (2001); Lee et al., Immunopharmacology 47:185-201 (2000); Adams et al., Bioorg. Med. Chem. Lett. 11: 2867-70 (2001); Regan et al., J. Med. Chem. 46:4676-4686 (2003); Laufer et al., J. Med. Chem. 45:2733-40 (2002); Colletti et al., J. Med. Chem. 46:349-52 (2003), Branger et al., J. Immunol. 168:4070-7 (2002), Henry et al., Bioorg. Med. Chem. Lett. 8:3335-40 (1998); Adams et al., Prog. Med. Chem. 38:1-60 (2001), Revesz et al., Bioorg. Med. Chem. Lett. 10:1261-4 (2000), Ottosen et al., J. Med. Chem. 46:5651-62 (2003); Thurmond et al., Eur. J. Biochem. 268:5747-54 (2001), Jackson et al., Curr. Top. Med. Chem. 2:1011-20 (2002); Jeohn et al., Neuroscience 114:689-97 (2002); Revesz et al., Bioorg. Med. Chem. Lett. 12:2109-12 (2002); Orchard, Curr. Opin. Drug Discov. Devel. 5:713-7 (2002); Nishikori et al., Eur. J. Pharmacol. 451:327-33 (2002); Foster et al., Drug News Perspect. 13:488-97 (2000); Boehm et al., Bioorg. Med. Chem. Lett. 11:1123-6 (2001); Hunt et al., Bioorg. Med. Chem. Lett. 13:467-70 (2003); de Laszlo et al., Bioorg. Med. Chem. Lett. 8:2689-94 (1998); McIntyre et al., Bioorg. Med. Chem. Lett. 12:689-92 (2002); Haddad et al., Curr. Opin. Investig. Drugs. 2:1070-6 (2002); Collis et al., Bioorg. Med. Chem. Lett. 11:693-6 (20001).

In one preferred embodiment, the ERK kinase inhibitor is U0126 or PD98059.

An ERK inhibitor according to this aspect of the present invention can be an ERK "direct inhibitor" which inhibits ERK intrinsic activity or expression (e.g., antisense and siRNA) or an ERK "indirect inhibitor" which inhibits the activity or expression of upstream components in the ERK signaling cascade, e.g., MEK, provided such upstream components are expressed in the lens epithelial cell, thereby inhibiting ERK activity. ERK inhibitors down-regulate the quantity or activity of ERK components (molecules). Inhibition of these cellular components can be achieved by a variety of mechanisms known in the art, including, but not limited to, binding directly to ERK 1 or ERK2 (e.g., an ERK-inhibitor compound binding complex, or substrate mimetic), binding directly to MEK1 or MEK2, or inhibiting expression of the ERK or MEK genes. Examples of inhibitors of the ERK pathway that may be used in accordance with the invention include, but are not limited to, Raf-1 inhibitors, such as GW5074, BAY 43-9006, and ISIS 5132 (Lackey, K. et al., Bioorg. Med. Chem. Lett., 2000, 10: 223-226; Lyons, J. F. et al., Endocrine-related Cancer, 2001, 8: 219-225; and Monia, B. P. et al., Nat. Med., 1996, 2(6): 668-675, respectively), (5-Iodo-3-[(3,5-dibromo4 hydroxyphenyl)methylene]-2 indolinone) and ZM 336372; and MEK1/2 inhibitors, such as PD98059, PD184352, U0126 and U0125 (Dudley D. T. et al., Proc. Natl. Acad. Sci. USA, 1995, 92: 7686-7689; Sepolt-Leopold J. S. et al., Nat. Med., 1999, 5: 810-816; and Favata M. F. et al., J. Biol. Chem., 273: 18623-18632, respectively). Both U0126 and PD98059 prevent phosphorylation of MEK1 by upstream kinases in a manner that appears to be substrate-directed (Davies, S. P. et al., Biochem. J., 2000, 351: 95-105; Ahn N. G. et al., Methods Enzymol., 2001, 332: 417-431). Based on recent evidence, it appears likely that PD98059, U0126, and PD184352 act as allosteric inhibitors, binding outside the ATP- and ERK1/2-binding sites on MEK1/2 and the modification of the three-dimensional structure of MEK1/2 renders it not phosphorylatable by upstream kinases (Davies, S. P. et al., 2001). Such a modification of MEK1/2 may also reduce their kinase activity towards ERK1/2; a high concentration of Uo126 and of PD184352 has been shown to inhibit MEK activity. A series of 3-cyano-4-(phenoxyanilo) quinolines with MEK inhibitory activity has also been developed by Wyeth-Ayerst (Zhang N. et al., Bioorg Med. Chem. Lett., 2000, 10: 2825-2828). Several resorcylic acid lactones having inhibitor activity toward MEK have been isolated from microbial extracts. For example, Ro 09-2210, isolated from fungal broth FC2506, and L-783,277, purified from organic extracts of *Phoma* sp. (ATCC 74403), are competitive with ATP, and the MEK1 inhibition is reversible (Williams D. H. et al., Biochemistry, 1998, 37: 9579-9585; and Zhao A. et al., J. Antibiot., 1999, 52: 1086-1094). Imidazolium trans-imidazoledimethyl sulfoxide-tetrachlororuthenate (NAMI-A) is a ruthenium-containing inhibitor of the phosphorylation of MEK, the upstream activator of ERK (Pintus G. et al., Eur. J. Biochem., 2002, 269: 5861-5870).

A peptide corresponding to the amino-terminal 13 amino acids of MEK1, a region involved in the association of ERK1/2 with MEK1, has been shown to specifically inhibit the activation of ERK1/2. It may be stearated, Ste-MEK113, or fused to the HIV-TAT membrane translocating peptide (MTP) via a glycine linker, MTPTAT-G-MEK113 (Kelemen B. R. et al., J. Biol. Chem., 2002, 277: 87841-8748). Purvalanol, one of the most potent cyclin-dependent kinase (CDK) inhibitors to date, has been shown to target ERK1 and ERK2 (Knockaert M. et al., Oncogene, 2002, 21: 6413-6424). 3-(2-Aminoethyl)-5-((4-ethoxyphenyl)methylene)-2,4-thiazolidinedione (Hancock, C. N., et al. 2005. J. Med. Chem. 48, 4586), Other ERK inhibitors that may be used in accordance with the present invention include those disclosed in U.S. patent publications nos. 20040082631, 20040048861, 20040029857, 20030225151, 20030195241, 20030060469, 20030049820, 20020151574, 20030158238, 20030092714, 20030040536, and 20020177618. Erk Kinase inhibitors are further described by Rubinfeld et al., Methods Mol. Biol. 250:1-28 (2004) and Kohno et al., Prog. Cell Cycle Res. 5:219-24 (2003).

An ERK inhibitor molecule can be a natural negative regulator of ERK or an ERK signaling molecule which has been modified to down-regulate or suppress ERK activity. Examples for such molecules include but are not limited to dominant-negative ERK [e.g., ERK1(K71R) and ERK2 (K52R)], dominant-negative Ras [e.g., Ras(S17N) and Ras (S17W)] and dominant-negative Raf-1 [e.g., Raf-1(K375W), Raf(C4B), Raf 301 and Raf(S621A)] and dominant-negative MEK [e.g., MEK1(K97A), MEK1(K97M), MEK2(K101A) and MEK1/2(KAMEK)], as is further detailed elsewhere [Cheng et al., 1999, JBC 274: 6553-8; Chen et al., 2000, Mol. Pharmacol. 57: 153-61; Salomoni et al; 1998, J. Exp. Med. 187: 1995-2007; Sun et al., 2002, J. Biol. Chem. 277: 1544-1552; Minden et al., 1994, Science 266: 1719-1723; Coso et al., 1995, Cell 81: 1137-1146; Bruder et al., 1992, Genes and Develop. 6: 545-556; Qureshi et al., 1991, J. Biol. Chem. 266: 20594-20597; Abbott and Holt, 1999, J. Biol. Chem. 274: 2732-2742; Gardner et al., 1994, Mol. Biol. Cell 5:193-201].

Examples of ERK inhibitors include pyrazole compositions and isoxazole compositions, the disclosure of isoxazole compositions herein incorporated by reference (Hale et al., (2002) U.S. Pat. No. 6,495,582). Identification of additional inhibitors may be accomplished by one of skill in the art through routine experimentation involving in vitro phosphorylation assays. For example, a compound library may be screened with a cascade assay that measures the phosphorylation of a substrate in the presence of purified kinase proteins. Order-of-addition experiments may be utilized to determine which kinase in the MAPK phosphorelay system is inhibited. A potential inhibitor may be added to a tube initially containing an upstream kinase in the MAPK/ERK cascade, buffer salts, and unlabelled ATP. Said upstream kinase is the kinase whose activity is to be assayed. The upstream kinase may be a MAPKK, MAPK, or ERK. If the upstream kinase to be assayed normally activates a downstream kinase, purified downstream kinase is then added along with a proper substrate and [γ-32P]ATP. If said upstream kinase is MAPKK or MAPK, then said downstream kinase is MAPK or ERK, respectively. If said upstream kinase is ERK, then only a proper substrate and [γ-32P]ATP need be added. Proper substrates for MEK and ERK may be ERK and CaD, respectively. Transfer of the [γ-32P] to the substrate may then be determined. In a second order-of-addition experiment, the potential inhibitor compound may be added to a tube containing both upstream and downstream purified kinase proteins, buffer salts, and unlabeled ATP. A proper substrate for the downstream kinase may then be added and transfer of the [γ-32P] to the substrate determined. Transfer in the second but not the first order-of-addition experiment is indicative that the compound is an inhibitor of said upstream kinase. This method was utilized in the identification of the MEK inhibitor PD 098059. Variations on this assay may be made, such as omission of the addition of labeled [γ-32P] ATP if another detection method such as antibody recognition is available. Order-of-addition experiments need not be done, as the inability of a kinase to transfer of a labeled phosphate to its substrate may serve as a direct indicator of kinase inhibition.

Members of the Src family include at least the following eight kinases in mammals: Src, Fyn, Yes, Fgr, Lyn, Hck, Lck, and Blk. These are nonreceptor protein kinases that range in molecular mass from 52 to 62 Kd. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. Biochemistry (Moscow) 65, 49-58 (2000).

As used herein, the language "Src family kinase inhibitor" is intended to include any inhibitor of one or more kinases within the Src family of kinases. In a preferred embodiment, one or more Src family kinase inhibitors is used in the methods and ocular devices of the present invention.

In one preferred embodiment the Src family kinase inhibitor PP1 (Molecular Cell, 1999, 3: 639-648) is used. In another preferred embodiment the Src family kinase inhibitor SKI606 (Cancer Research, 2003, 63: 375) is used. In another preferred embodiment, the Src family kinase inhibitor AZD0530 (AstraZeneca, London UK) is used. In another preferred embodiment, the Src family kinase inhibitor SU6656 is used (Blake, R. A. et al. 2000. Mol. Cell. Biol. 20: 9018-9027)

Src family kinase inhibitors useful in the methods and ocular implants of the present invention include, but are not limited to, for example, International Patent Applications WO 96/10028; WO 97/07131; WO 97/08193; WO 97/16452; WO 97/28161; WO 97/32879; WO 97/49706; WO 01/94341; WO 02/16352; WO 02/30924; WO 02/30926; WO 02/34744; WO 02/085895; WO 02/092577; WO 02/092578; WO 02/092579; WO 03/008409 and co-pending International Application PCT/GB03/04703; WO 03/013540 (particularly the compounds disclosed therein by way of Formulae I to VIII and compounds based on Formulae VII and VIII but wherein the 2,6-dimethylphenyl group is replaced by a 2,6-dichlorophenyl or a 2-chloro-6-methylphenyl group); 4-amino-5-(3-methoxyphenyl)-7-{4-[2-(2-methoxyethylamino)ethoxy]phenyl}pyrrolo[2,3-d]pyrimidine and 4-amino-5-(3-methoxyphenyl) 7-(4-{2-[di-(2-methoxyethyl)amino]ethoxy}phenyl)pyrrolo[2,3-d]pyrimidine which are obtainable by methods described in International Patent Application WO 96/10028; 2-(2,6-dichloroanilino)-6,7-dimethyl-1,8-dihydroimidazo[4,5-h]isoquinolin-9-one and 2-(2,6-dichloroanilino)-7-[(E)-3-diethylaminoprop-1-enyl]-6-methyl 1,8-dihydroimidazo[4,5-h]isoquinolin-9-one which are obtainable by methods described in Journal Medicinal Chemistry, 2002, 45: 3394; 1-[6-(2,6-dichlorophenyl)-2-(4-diethylaminobutyl)pyrido[2,3-d]pyrimidin-7-yl]3-ethylurea which is obtainable by methods described in Journal Medicinal Chemistry, 1997, 40: 2296-2303 and Journal Medicinal Chemistry, 2001, 44, 1915; certain 4-anilino-3-cyanoquinoline derivatives (Journal Medicinal Chemistry, 2001, 44: 822-833 and 3965-3977); PD166285 (J. Pharmacol. Exp. Ther., 1997, 283: 1433-1444); PD162531 (Mol. Biol. Cell, 2000, 11: 51-64); PD166326 and PD180970 (Biochem. Pharmacol., 2000, 60: 885-898); PD173955 (Cancer Research, 1999, 59; 6145-6152); PD173952 (Blake, R. A. et al. 2000. Mol. Cell. Biol. 20: 9018-9027); Dasatinib or BMS354825 (Lombardo et al. 2004. J Med. Chem. 47:6658-6661); the pyrazolopyrimidine class of Src family kinase inhibitors, such as 4-amino-5-(4-methylphenyl)-7-(t-butyl-) pyrazolo[3,4-d-]pyrimidine (AGL 1872), 4-amino-5-(4-chlorophenyl)-7-(t-butyl)pyrazolo[3,4-d-]pyrimidine (AGL 1879), and the like; the macrocyclic dienone class of Src family kinase inhibitors, such as Radicicol R2146, Geldanamycin, Herbimycin A, and the like; the pyrido[2,3-d]pyrimidine class of Src family kinase inhibitors; the 4-anilino-3-quinolinecarbonitrile class of Src family kinase inhibitors; tyrphostin-derived inhibitors, which are derivatives of benzylidenemalonitrile (Ramdas et al., 1995, Archives of Biochemistry and Biophysics 323:237-242); derivatives of pyrazolopyrimidine PP1 (4-amino-5-(4-methylphenyl)-7-(t-butyl)pyrazolo[3,4-d]pyrimidine (Hanke et al., 1996, J. Biol. Chem. 271:695-791); angelmicin B and derivatives thereof (Yokoyama et al., 1996, Leukemia Research 20:491-497); compounds described in J Bone Mineral Research, 1999, 14: (Suppl. 1) S487, Molecular Cell, 1999, 3: 639-647, Journal Medicinal Chemistry, 1997, 40: 2296-2303, Journal Medicinal Chemistry, 1998, 41: 3276-3292 and Bioorganic & Medicinal Chemistry Letters, 2002, 12: 1361 and 3153.

Additional Src family kinase inhibitors useful in the methods and devices of the present invention are described in, for example, International Patent Applications WO 05/013983, WO 02/079192, WO 03/000188, WO 03/000266, WO 03/000705, WO 02/083668, WO 02/092573, WO 03/004492, WO 00/49018, WO 03/013541, WO 01/00207, WO 01/00213, WO 01/00214 and U.S. Patent Applications 2005/0096298, 20040266855, 2004/0204582, 2004/0167198, 2004/0014676, 2003/0207902, 2003/0119819 and 2002/0132819.

In another embodiment of the present invention, small peptides which compete with larger phosphotyrosine peptides for binding to the Src kinase protein may be used to inhibit Src family kinases, in particular small phosphotyrosine containing peptide ligands, 5 to 6 amino acids, which are able to compete with larger phosphotyrosine-containing peptides and protein ligands for binding to SH2 domains, thereby inhibiting the Src family kinases. Another embodiment of the present invention includes small peptides which correspond to catalytic or enzymatic domains of Src kinase and would compete with Src kinase, inhibiting the activation of downstream components of the Src kinase signaling cascade. Another embodiment includes the use of larger polypeptides that inhibit Src kinase activity including, but not limited to, Csk (carboxyl-terminal Src kinase) which is a specific physiologic inhibitor of Src kinase. Further examples of larger polypeptides that inhibit Src kinase activity include, for example, Src dominant-negative mutants, i.e., Srck-(Barone et al., 1995, Nature 378:509-512) and Fyn dominant-negative mutants (Twamley-Stein et al., 1993, Proc. Natl. Acad. Sci. USA 90:7696-7700).

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All references cited throughout this specification are herein incorporated by reference in their entirety.

EXAMPLES

Example 1

Figure 1:
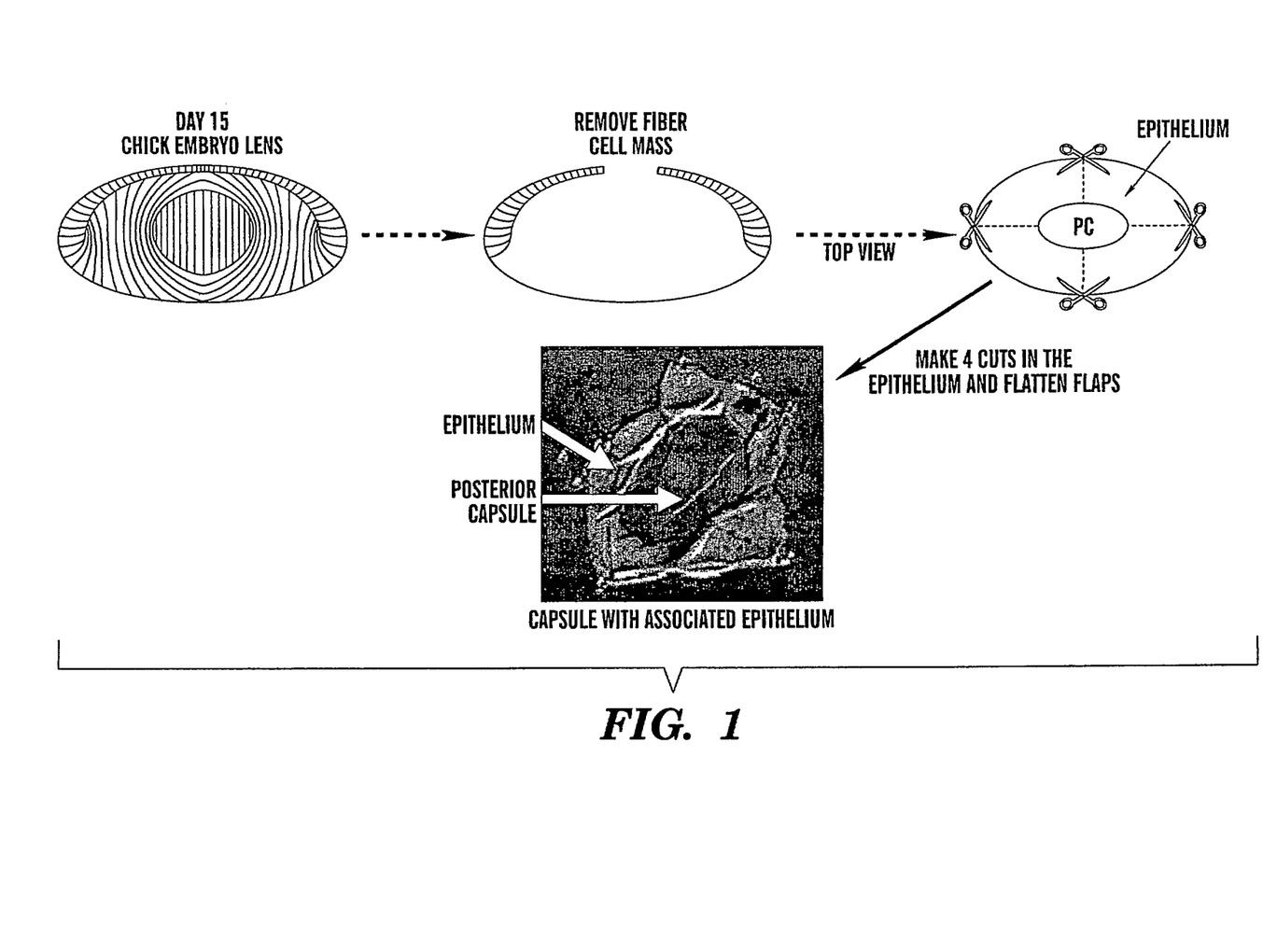
FIG. 1 shows the establishment of a chick embryo lens "Capsular Bag Model" to study mechanisms of PCO induction and prevention
Figure 2:
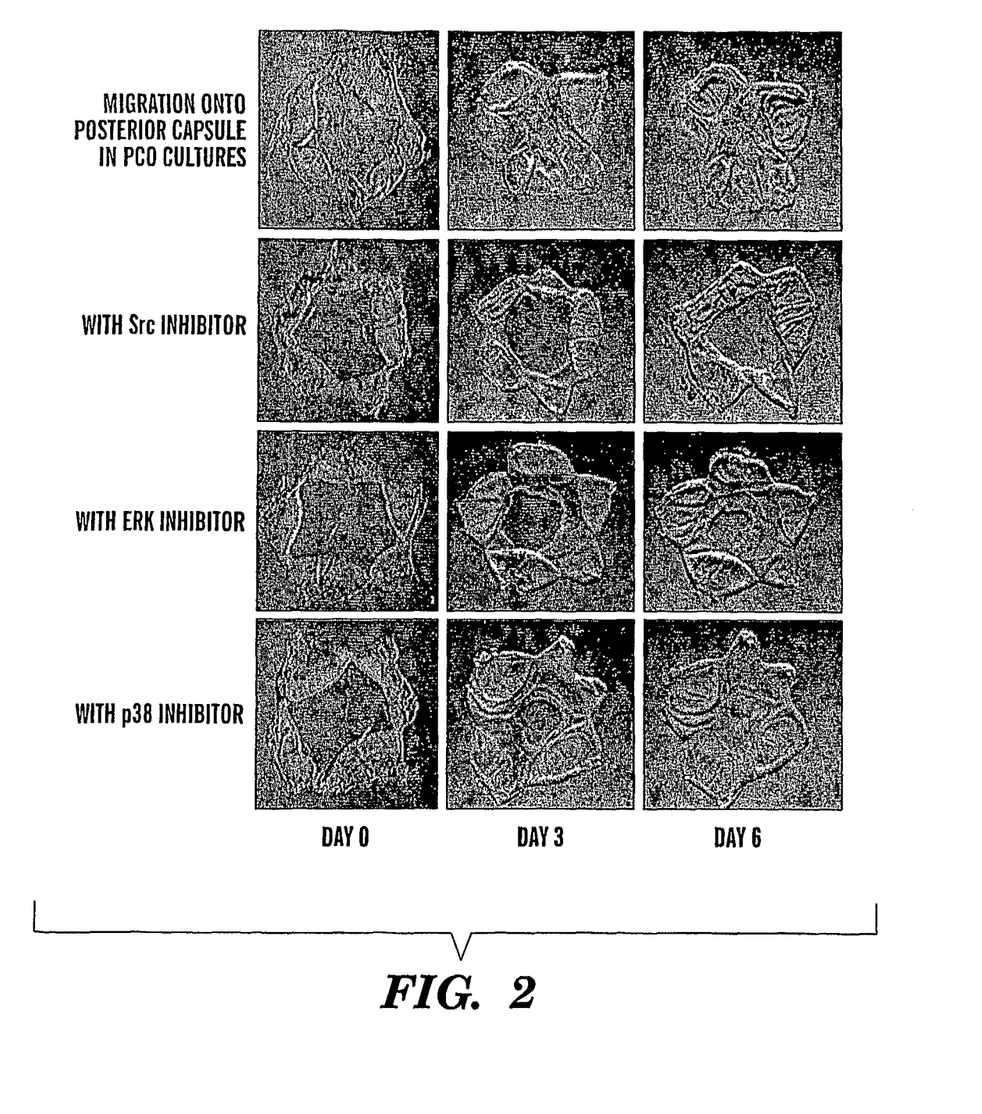
FIG. 2 shows migration of the lens epithelial cells from the equatorial epithelium onto the posterior capsule causing the capsule to wrinkle in culture. Inhibitors of both ERK and p38 kinases delayed but did not block epithelial cell migration onto the posterior capsule. Migration of the lens epithelial cells across the posterior capsule was completely blocked in the presence of a Src kinase specific inhibitor.

The purpose of the experiments described herein was to examine the signaling mechanisms involved in cell migration and epithelial to mesenchymal transformation (EMT) during the development of posterior capsule opacification (PCO). Establishment of a Chick Embryo Lens "Capsular Bag Model" to Study Mechanisms of PCO Induction and Prevention The capsular bag culture has proven an important model for the study of PCO. The procedure, developed by Liu et al. (Invest Opthalmol V is Sci. 1996. 37:906-914) for human lenses, mimics the preparation of the capsule in cataract surgery. We have adapted this model to the embryonic day 15 chick lens because it provides an unlimited source of tissue, making it feasible to investigate the mechanisms that induce PCO and identify likely targets for its prevention. Briefly, the fiber cell mass is removed (FIG. 1), and the lens capsule with lens epithelial cells still attached, the capsular bag, placed in culture. Cuts are made in the anterior region of the capsule and the resultant flaps flattened onto the culture dish. This provides an unimpeded view of the movement of lens epithelial cells onto the empty posterior capsule. In these cultures, as occurs in PCO, the lens epithelial cells migrate from their point of origin, the equatorial epithelium, onto the posterior capsule and cause the capsule to wrinkle (FIG. 2, top panels). While the surface of the posterior capsule is covered with cells within 3 days, at this time in culture there is no expression of EMT markers such as α smooth muscle actin (α-SMA) or fibronectin. In contrast, at 6 days in culture, when the posterior capsule appeared wrinkled (FIG. 2), the cells expressed high levels of α SMA and fibronectin (FIG. 3, controls), evidence that the cells had undergone an EMT.

Inhibition of Src Kinases Prevents Lens Epithelial Cell Migration onto the Posterior Capsule and EMT Both migration of the lens epithelial cells across the posterior capsule (FIG. 2) and expression of both α-SMA and fibronectin (FIG. 3) were completely blocked when the capsular bag cultures were grown in the presence of a Src kinase specific inhibitor. This single exposure to the Src inhibitor was sufficient to block migration and EMT for 18 days, the maximal time we have observed the capsular bags in culture. Our data shows that Src kinases are involved in signaling both the migration of lens epithelial cells onto the posterior capsule and their EMT. This result provides great hope that PCO can be prevented simply by exposing the lens epithelial cells in the equatorial zone to a pharmaceutical inhibitor of the signaling pathways that induce migration and/or EMT during cataract surgery. To prevent PCO, drug therapies like the Src kinase inhibitor can be delivered directly to the interior of the lens capsule at the time of cataract surgery.

Figure 4A:
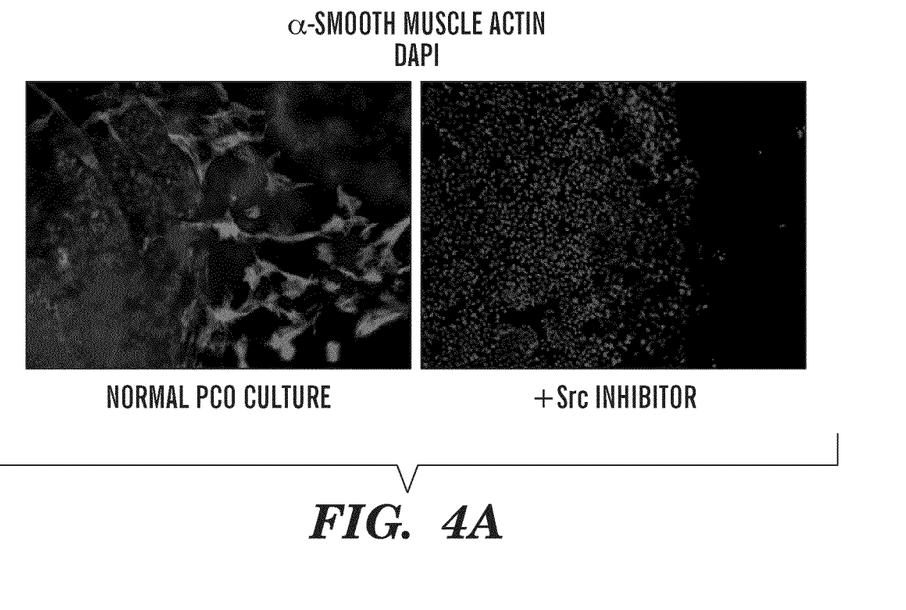
FIG. 4A shows that after 6 days in culture, α-SMA positive cells with a mesenchymal morphology are found in all regions of the capsular surface. However, in the presence of a Src specific inhibitor, no α-SMA positive cells emerge from the epithelium.
Figure 4B:
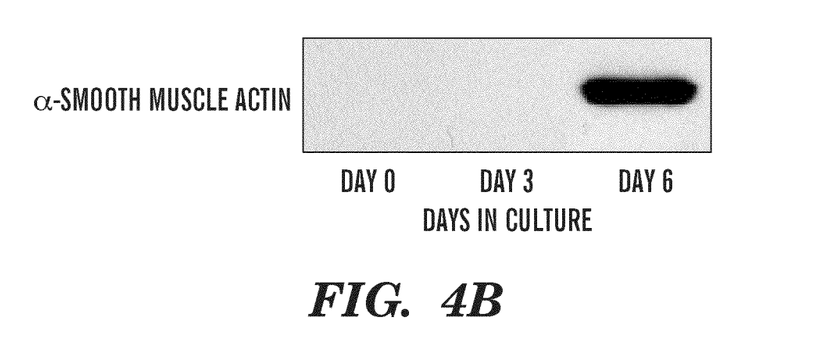
FIG. 4B shows α-SMA is not expressed until day 6 in culture by western blot.

Emergence of Mesenchymal Cells Occurs after the Migration of Lens Epithelial Cells onto the Posterior Capsule and is Prevented by Inhibiting Src Kinase Activity In the PCO cultures lens epithelial cells begin to migrate across the posterior capsule within the first day in culture and cover the entire posterior capsule by day 3 in culture. However, at culture day 3 no α SMA positive cells could be detected either by immunolocalization or by protein analysis. In contrast at 6 days in culture, when significant wrinkling of the posterior capsule is observed, α SMA expressing cells with a mesenchymal morphology are found in all regions of the capsular surface (FIG. 4). From these studies we have concluded that EMT does not occur until after the lens epithelial cells had migrated across the posterior capsule. In the presence of a Src specific inhibitor, no α-SMA positive cells emerge from the epithelium (FIG. 4).

Inhibition of ERK and P38 Kinases Blocks EMT But not Cell Migration

Figure 3:
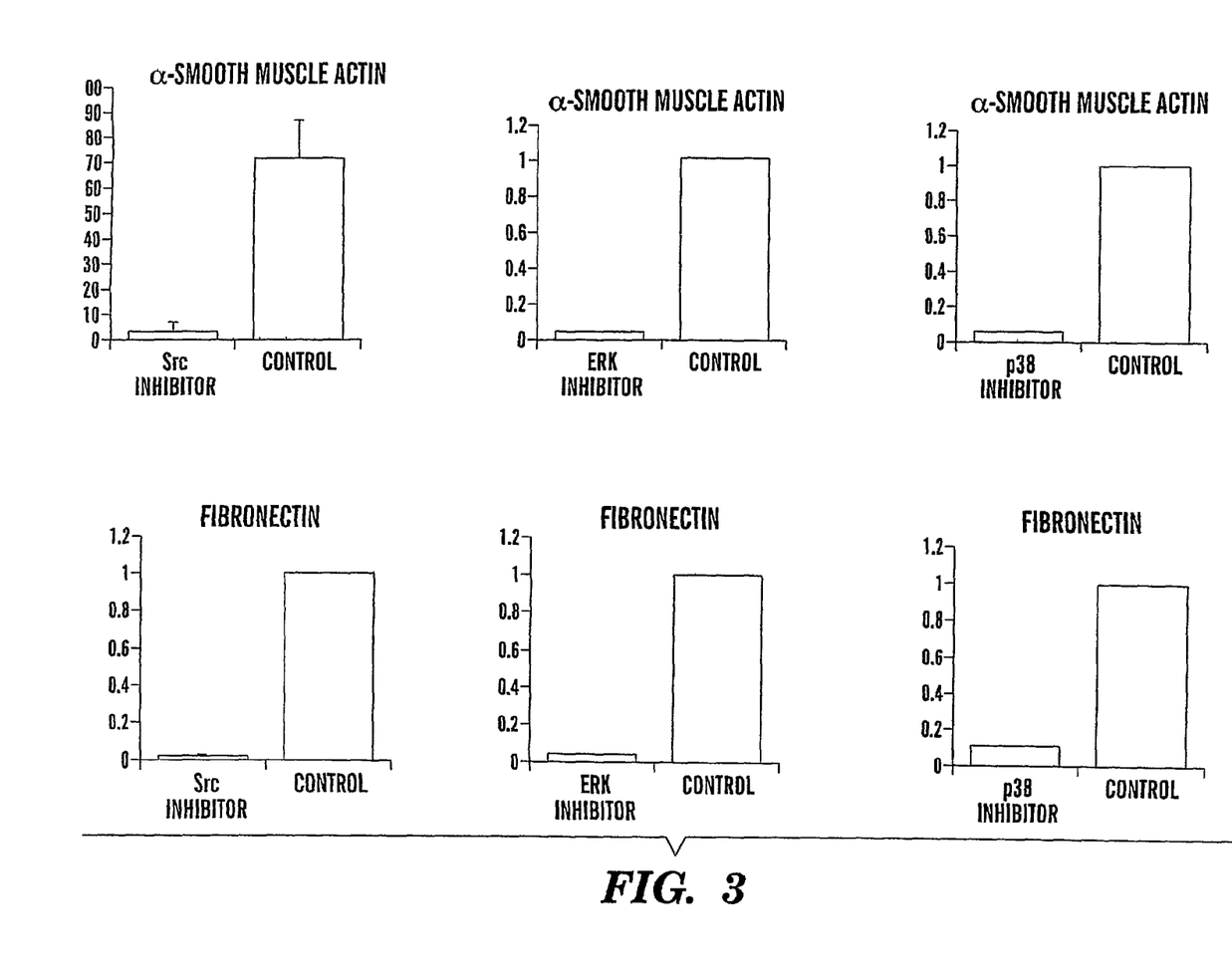
FIG. 3 shows α-smooth muscle action and fibronectin expression are blocked in the presence of ERK, p38 or Src kinase inhibitors.

Inhibitors of both ERK and p38 kinases delayed but did not block epithelial cell migration onto the posterior capsule (FIG. 2). However, both of these inhibitors completely blocked the emergence of α SMA and fibronectin positive cells (FIG. 3). The dramatic affect of these inhibitors on the EMT of lens cells without affecting cell migration supports the hypothesis that migration and EMT are distinct events in the development of PCO and that the EMT of lens epithelial cells does not occur until after they have migrated onto the posterior capsule.

Chick lens capsular bags prepared by sham cataract surgery were placed in culture. Cell movement across the posterior capsule was documented microscopically. EMT was determined by expression of α smooth muscle actin (α-SMA) and fibronectin. Mechanisms of migration and EMT were examined by inhibiting Src, ERK and p38 kinases using PP1, UO126 and SB203580, respectively.

PCO, the major complication of cataract surgery, results from migration of residual lens epithelial cells onto the posterior capsule, their EMT and the subsequent wrinkling of the posterior capsule. In our PCO cultures lens cells covered the posterior capsule within three days, but no EMT markers were detected. By six days in culture, α SMA and fibronectin were highly expressed and the posterior capsule was wrinkled. α SMA expressing cells, all with a fibroblastic morphology, emerged both in the region of origin of the epithelial cells and in cells along the posterior capsule. Src, ERK and p38 kinases were examined for their role in lens cell migration vs. EMT in PCO. Inhibition of Src kinases blocked lens cell migration and EMT. Inhibitors of ERK and p38 kinases had little effect on cell migration but efficiently blocked EMT.

In PCO the migration of lens epithelial cells onto the posterior capsule precedes EMT. Signaling pathways for migration require Src, not ERK or p38 activity; EMT requires the function of Src, ERK and p38 kinases.

Example 2

In PCO, the expression of the EMT marker α-SMA does not occur until after lens cells migrate across the posterior capsule (FIG. 4B). Migration is apparent by day 6 in PCO cultures (FIG. 4A).

Figure 5:
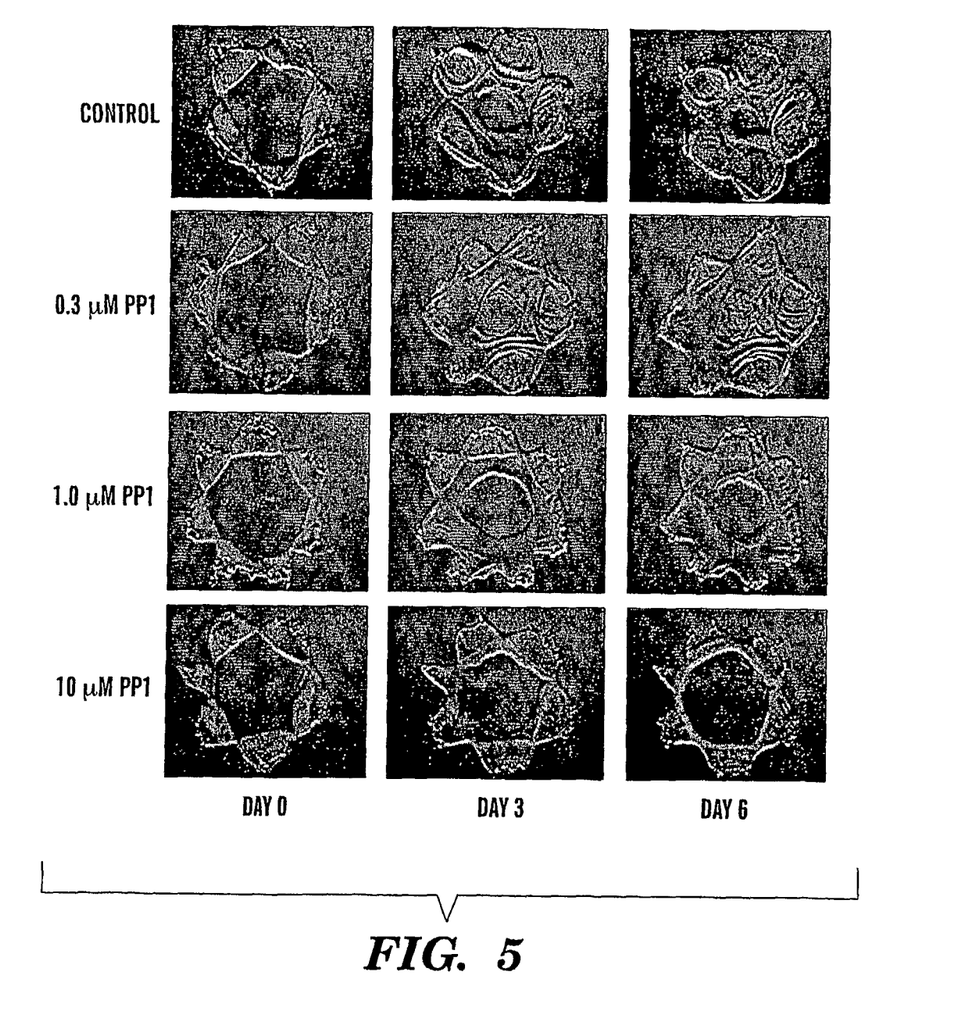
FIG. 5 shows the Src inhibitor PP1 is effective in blocking cell migration. Cultures were treated with 0 μM, 0.3 μM, 1.0 μM, and 10 μM of PP1 and images taken at day 0, 3, and 6 of culture.

Results from dose-response tests for the Src inhibitor PP1 in blocking cell migration in the PCO model are shown in FIG. 5. Dosage as low as 1.0 µM PP1 is effective at blocking cell migration associated with PCO.

Figure 6:
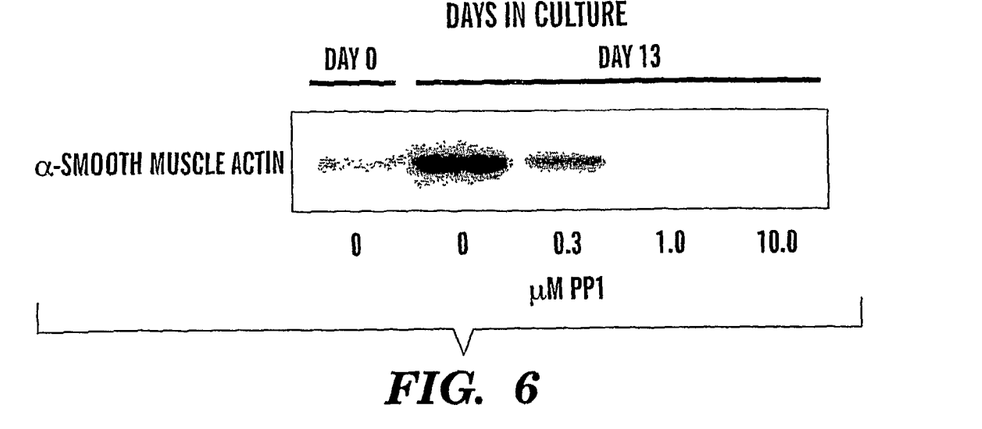
FIG. 6 shows that α-SMA expression is inhibited at doses as low as 0.3 µM of PP1. α-SMA expression was monitored at day 0 and day 13 under culture conditions of 0 µM, 0.3 µM, 1.0 µM, and 10.0 µM of PP1.

Inhibition of EMT associated with PCO by Src inhibitor PP1 is effective at doses as low as 0.3 µM as evidences by inhibition of the expression of the EMT marker α-smooth muscle actin (FIG. 6).

Figure 7:
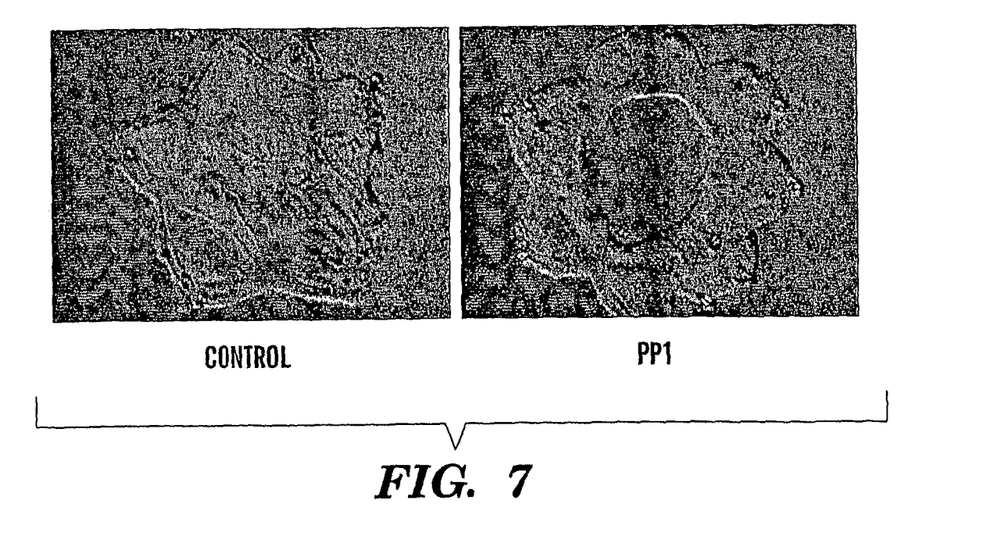
FIG. 7 shows that a single dose of PP1 was sufficient to inhibit PCO for at least 14 days in culture.

The Src inhibitor PP1 is effective in blocking PCO long-term. PCO was inhibited in cultures exposed to the Src inhibitor PP1 only at time 0 and grown for 14 days in culture (FIG. 7). A single dose of PP1 was sufficient to inhibit PCO.

The references cited throughout the application are incorporated herein by reference in their entirety.

The invention claimed is:

1. A method to treat posterior capsular opacification, comprising administering a therapeutically or prophylactically effective amount of pharmaceutical composition comprising at least one kinase inhibitor, wherein the kinase inhibitor inhibits p38 kinases, ERK kinases, and/or Src family kinases.

2. The method of claim 1, wherein the kinase inhibitor is administered on an ocular device.

3. The method of claim 2, wherein the ocular device is an intraocular lens implant.

4. The method of claim 1, wherein the kinase inhibitor is administered as an ocular wash.

5. The method of claim 1, wherein the composition is an extended-release formulation.

6. The method of claim 1, wherein the p38 inhibitor is SB203580 or SB202190.

7. The method of claim 1, wherein the ERK kinase inhibitor is U0126 or PD98059.

8. The method of claim 1, wherein the Src family kinase inhibitor is 4-amino-5-(4-methylphenyl)-7-(t-butyl)pyrazolo[3,4-d]pyrimidine, 4-amino-5-(4-chlorophenyl)-7-(t-butyl)pyrazolo[3,4-d]pyrimidine, SKI606, or SU6656.

9. An ocular device coated with one or more Src family kinase, p38 and/or ERK kinase inhibitors.

* * * * *